(12) United States Patent
Evans et al.

(10) Patent No.: US 10,406,024 B2
(45) Date of Patent: Sep. 10, 2019

(54) WEARABLE TEMPERATURE THERAPY SYSTEM AND METHOD

(71) Applicant: RecoverX, Inc., San Francisco, CA (US)

(72) Inventors: Daniel Royal Evans, San Francisco, CA (US); Alexander Joseph Aguiar, San Francisco, CA (US)

(73) Assignee: RecoverX, Inc., San Diego, CA (US)

( * ) Notice: Subject to any disclaimer, the term of this patent is extended or adjusted under 35 U.S.C. 154(b) by 0 days.

(21) Appl. No.: 15/818,308

(22) Filed: Nov. 20, 2017

(65) Prior Publication Data
US 2018/0147086 A1 May 31, 2018

Related U.S. Application Data

(60) Provisional application No. 62/427,305, filed on Nov. 29, 2016, provisional application No. 62/503,050, filed on May 8, 2017.

(51) Int. Cl.
*A61F 7/00* (2006.01)
*A61F 7/02* (2006.01)

(52) U.S. Cl.
CPC .............. *A61F 7/02* (2013.01); *A61F 7/007* (2013.01); *A61F 2007/0042* (2013.01);
(Continued)

(58) Field of Classification Search
CPC ...... A61F 2007/0042; A61F 2007/0075; A61F 2007/0078; A61F 2007/0096;
(Continued)

(56) References Cited

U.S. PATENT DOCUMENTS

| 4,962,761 | A | * | 10/1990 | Golden ..................... A61F 7/02 165/46 |
| 5,080,089 | A | | 1/1992 | Mason et al. |
| 5,800,490 | A | * | 9/1998 | Patz ........................ A61F 7/007 607/108 |
| 5,865,841 | A | | 2/1999 | Kolen et al. |
| 5,871,526 | A | | 2/1999 | Gibbs et al. |
| 6,818,012 | B2 | | 11/2004 | Ellingboe |
| 8,425,579 | B1 | | 4/2013 | Edelman et al. |

(Continued)

FOREIGN PATENT DOCUMENTS

CA      2356993      7/2000

OTHER PUBLICATIONS

Jordan, et al., Electric Hot/Cold Wrap. Dec. 2010 [retrieved from the internet: ,URL: http://www.mie.neu.edu/mie/capstone/mechanical-engineering-capstone-projects.

*Primary Examiner* — Kaitlyn E Smith
*Assistant Examiner* — Yasamin Ekrami
(74) *Attorney, Agent, or Firm* — Jeffrey Schox; Diana Lin

(57) ABSTRACT

A wearable cooling and heating system for placement at a body region of a user, including a retention mechanism defining an internal side, and an external side; a temperature modulation subsystem, coupled to the retention mechanism, including a temperature-controllable substrate arranged at the internal side of the retention mechanism, a shield, defining a shield cavity, the shield arranged at the external side of the retention mechanism and coupled to the temperature-controllable substrate, and a heat exchanger in thermal contact with the temperature-controllable substrate and arranged within the shield cavity; a control module, retained by the retention mechanism, communicatively coupled to the temperature modulation subsystem, wherein the temperature modulation subsystem is operable between a cooling mode and a heating mode by the control module, wherein the cooling mode includes generating a low temperature at the temperature-controllable substrate, and wherein the heating mode includes generating a high temperature at the temperature-controllable substrate.

19 Claims, 10 Drawing Sheets

(52) U.S. Cl.
CPC .............. *A61F 2007/0075* (2013.01); *A61F 2007/0078* (2013.01); *A61F 2007/0093* (2013.01); *A61F 2007/0094* (2013.01); *A61F 2007/0096* (2013.01); *A61F 2007/0228* (2013.01); *A61F 2007/0231* (2013.01); *A61F 2007/0233* (2013.01); *A61F 2007/0244* (2013.01); *A61F 2007/0246* (2013.01); *A61F 2007/0295* (2013.01); *A61F 2007/0296* (2013.01)

(58) Field of Classification Search
CPC ...... A61F 2007/0228; A61F 2007/0231; A61F 2007/0244; A61F 2007/0295
See application file for complete search history.

(56) References Cited

U.S. PATENT DOCUMENTS

| | | | |
|---|---|---|---|
| 2008/0046047 A1* | 2/2008 | Jacobs | A61F 7/007 607/108 |
| 2008/0188915 A1 | 8/2008 | Mills et al. | |
| 2010/0198322 A1 | 8/2010 | Joseph et al. | |
| 2012/0179231 A1 | 7/2012 | Dewaegenaere | |
| 2013/0085552 A1* | 4/2013 | Mandel | A61F 7/007 607/99 |
| 2013/0087180 A1 | 4/2013 | Stark et al. | |
| 2015/0101788 A1* | 4/2015 | Smith | G01K 1/143 165/201 |

* cited by examiner

WEARABLE TEMPERATURE THERAPY SYSTEM AND METHOD

CROSS-REFERENCE TO RELATED APPLICATIONS

This application claims the benefit of U.S. Provisional Application Ser. No. 62/503,050, filed 8 May 2017 and U.S. Provisional Application Ser. No. 62/427,305, filed 29 Nov. 2016, which are each incorporated herein in their entirety by this reference.

TECHNICAL FIELD

This invention relates generally to the physical therapy assistive device field, and more specifically to new and useful wearable temperature therapy systems and methods in the field of physical therapy assistive devices.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1—Overview

Figure 1:
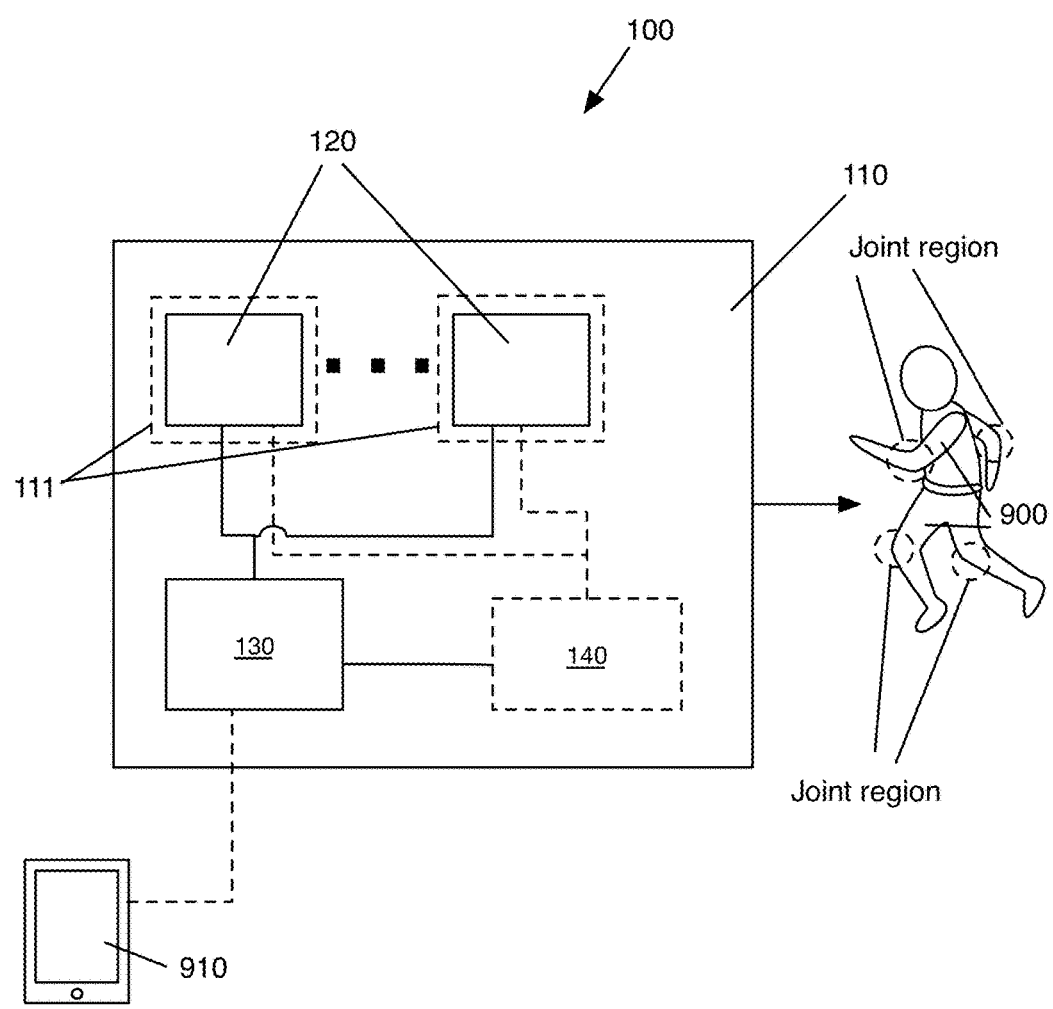
FIG. 1 is a schematic of a variation of an embodiment of the system.

As shown in FIG. 1, an embodiment of a wearable cooling and heating system includes a retention mechanism 110, a temperature modulation subsystem 120 retained by the retention mechanism 110, and a control module 130 communicatively coupled to the temperature modulation subsystem 120 and retained by the retention mechanism 110. The system can include a power supply module 140 retained by the retention mechanism 110 and electrically coupled to the temperature modulation subsystem 120 and the control module 130, a client application 131 executing at a mobile device 910 in communication with the control module 130, and any other suitable components.

The wearable cooling and heating system functions to provide temperature regulated cold and/or hot therapy to a body region of a user 900, and in specific examples can provide both cold and hot therapy to a body region of the user, using the same device, with rapid transitions between heat and cold therapy provision modes (e.g., heating mode, cooling mode, etc.) of operation. The system can also function to regulate the temperature of the hot or cold therapy based on received control instructions (e.g., from a mobile application-based controller, a mobile computing platform, a client application execution thereon, etc.). The system can also function to monitor and/or track parameters of therapy provision, such as the temperature of the hot or cold therapy being provided, the power and/or energy usage of the system during therapy provision, and any other suitable parameters. The system can also function to track user data such as frequency of use (e.g., daily, hourly, monthly, etc.), duration of use (e.g., total duration in minutes, duration on a per-operating-mode basis, duration on a per-contiguous-use basis, etc.) and therapy selection (e.g., heat therapy, cold therapy), and provide tracked user data to an entity (e.g., the user, a physical therapist associated with the user, etc.), in order to guide automated modes of therapy provision to the user.

The system is preferably communicatively coupled with a remote computing system (e.g., a mobile device of the user, a remote server, etc.). The system can preferably receive and/or transmit instructions, preferences, and/or other suitable data. In some examples, the system can be connected to an external power source for power provision (e.g., a wall outlet, an AC-DC converter, etc.). The external power source can provide power directly (e.g., provide the sole source of power to the temperature modulation subsystem and/or other system components), indirectly (e.g., to charge a battery of the power supply module), in a supplementary manner (e.g., as backup power in the event of power supply module failure), or in any other suitable manner. However, the system can be otherwise suitably coupled to related systems.

The system preferably includes a wearable device that can be positioned at a musculoskeletal region of the user (e.g., a knee region, a lower back region, an elbow region, etc.). However, the system can additionally or alternatively include multiple instances of the wearable device in the same or different configurations, that can be positioned at disparate regions of the user (e.g., a first knee region, a second knee region, a lower back region, any other suitable musculoskeletal region, any other suitable body region, etc.). The system can preferably be placed around a knee region of a user, arranging one or more temperature modulation subsystems proximal a knee cap region of a user in a pattern defined by the retention mechanism 110. Additionally or alternatively, the system can be placed around a torso region of a user, positioning the temperature modulation subsystem(s) proximal another musculoskeletal region (e.g., a lower back region).

2—Benefits

Variations of the system and/or method of use can confer several benefits and/or advantages. Conventional cold therapy devices, such as ice, gel packs, and chemical cold packs typically have a limited duration of usefulness before they become ineffective and/or must be decommissioned prior to re-use. Gel packs or ice are typically too cold, and when applied directly to the person's skin they can cause irritation and blisters. Therefore, some doctors recommend placing a towel or other barrier over the injured area before applying the ice or gel pack in order to mitigate the effects of undesirable low temperatures.

Heat therapy devices such as electric heating pads, microwavable gels, and chemical hot packs typically require an external power source such as an electric outlet, or microwave. Due to the limitations of current cold and hot therapy devices, it is difficult for these products to be portable or used more than once. Conventional systems and methods are not portable since they depend on immobile heating and/or cooling systems to externally heat and/or cool system elements (e.g., a refrigerator, a microwave oven). In using such systems, an injured user can often be required to get up from a resting position in order to prepare these therapy devices, remain at home or in a clinical setting where external heating/cooling systems are accessible, and/or be subject to similar inconveniences. This inconvenient preparation process disrupts the rest required for proper recovery, and can contribute to unnecessary lengthening of recovery times. As such, the system(s) and method(s) described herein can provide several benefits.

First, variations of the system can be portable and thereby enable hot and/or cold therapy application independent of external heating and/or cooling systems (e.g., the system can be powered by a rechargeable power supply such as a battery).

Second, variations of the system can apply heat and cold therapy alternately, using a single temperature modulation subsystem that is capable of generating and applying both hot and cold temperatures at the same user-interfacing surfaces. In related variations, the system can apply both hot and cold therapy simultaneously at different regions of the user (e.g., corresponding to distinct temperature modulation subsystems).

Third, variations of the system can maintain continuous, precisely managed therapeutic temperatures (e.g., between 32-60° F. for cold therapy, between 70-113° F. for hot therapy, any other suitable temperatures) through active temperature control (e.g., including selecting a temperature at a mobile device of the user).

Fourth, variations of the system can enable rapid application of hot and/or cold therapy without substantial lead time (i.e., time taken to externally heat and/or cool the system), and maintain the hot and/or cold therapy for a desired (e.g., selectable, controllable) time period (e.g., 10-20 minutes, any other suitable time period).

Fifth, variations of the system can improve injury healing and injury recovery through expeditious and controlled application of hot and/or cold therapy, and through promoting ease of use (e.g., reinforcing proper user behavior as recommended by a physical therapist or other injury therapy professional).

However, variations of the system and/or method of use can confer any other suitable benefits.

3—System

As noted above, embodiments of the wearable cooling and heating system can include a retention mechanism 110, a temperature modulation subsystem, a control module 130, and a power supply module 140. However, the wearable cooling and heating system can additionally or alternatively include any other suitable components.

The system functions to generate a high temperature and/or a low temperature at a contact surface in direct thermal contact with a body region of the user. A high temperature is preferably a temperature that is higher than a skin temperature of the body region of the user, and is preferably determined (e.g., by the control module, by the user, by an entity associated with the user, etc.) and/or applied to provide the therapeutic benefits of such a temperature (e.g., circulation promotion, muscle relaxation, etc.). In specific examples, the high temperature can be a temperature between 100-120° F., 102-115° F., 108-109° F., or any other suitable temperature range (e.g., above body temperature). The low temperature is preferably a temperature that is lower than a skin temperature of the body region of the user, and is preferably determined (e.g., by the control module, by the user, by an entity associated with the user, etc.) applied to provide the therapeutic benefits of such a temperature (e.g., pain relief, inflammation reduction, circulation modulation, etc.). In specific examples, the low temperature can be a temperature between 45-65° F., 49-61° F., 50-51° F., and any other suitable temperature range (e.g., at or below body temperature). However, both the high and low temperature can correspond to any suitable actual or perceived (e.g., wet bulb) temperature within or outside the aforementioned ranges. The system is preferably capable of controlling both the high and low temperature to within one tenth of one degree Fahrenheit, but can additionally or alternatively be capable of controlling both the high and low temperature at any suitable precision.

3.1—Retention Mechanism

The retention mechanism 110 functions to retain the temperature modulation subsystems at regions of the user where hot and/or cold therapy is desired. The retention mechanism 110 can also function to retain other components of the system (e.g., the control module, the power supply module, etc.). The retention mechanism no can also function to provide electrical pathways between the temperature modulation subsystem 120 and other system electronics (e.g., of the control module, of the power supply module, etc.). The retention mechanism no can also function to provide conduits for the routing of electrical pathways (e.g., wires) between electronic components. The retention mechanism no can also function to provide passive compression and/or support to a body part of a user (e.g., as a compression sleeve, a brace, etc.). The retention mechanism no includes one or more retention regions (e.g., corresponding to a number of components to be retained, such as one or more temperature modulation subsystems, control modules, etc.), and can optionally include temporary couplers (e.g., electromechanical ports that reversibly couple with modules and/or portions of the temperature modulation subsystem, control module, power supply module, etc.). The retention mechanism 110 is preferably directly coupled to the temperature modulation subsystems (e.g., physically retains the temperature modulation subsystems), but can be otherwise suitably coupled to other system components.

The retention mechanism 110 preferably includes (e.g., is fabricated from) fabric and/or other suitable flexible textile material (e.g., neoprene, synthetic fabric, natural material-based fabric, etc.). Alternatively, the retention mechanism no can include material with a varying degree of rigidity (e.g., as in a cast or brace), and can be composed of one or more of: a metallic material, a polymeric material, a ceramic material, and any other suitable material. In a further alternative, the retention mechanism 110 can integrate support structures that can transition between different mechanical behaviors (e.g., as in shape-memory materials). The retention mechanism no can be washable (e.g., not damaged or denatured through contact with water, particular water at a temperature within the range of temperatures commonly used while washing, and/or with soaps and detergents that are typically used in residential and commercial washing machines). The retention mechanism 110 can additionally or alternatively be dryable (e.g., resilient to air temperatures in the range of temperatures commonly used while drying without excessive damage and/or wear to material of the retention mechanism).

Figure 2:
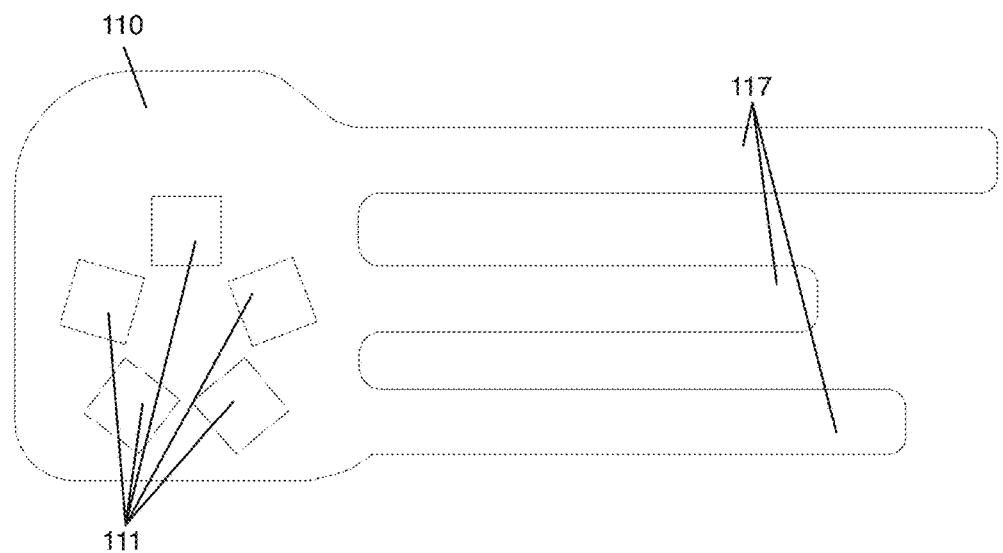
FIG. 2 is a schematic of a variation of the retention mechanism of the system.

In a first variation, as shown in FIG. 2, the retention mechanism 110 is a substantially flat, flexible substrate that includes multiple flexible appendages that are configured to wrap around the anatomy of the user. For example, as shown in FIG. 2, the retention mechanism 110 can include an ovoid substrate that defines a broad face and includes three pairs of appendages, wherein each pair is configured to wrap around the anatomy of the user and couple to one another in order to secure the system to the user (e.g., via buckles, hook-and-loop fasteners, any other suitable male and/or female fasteners or couplers, etc.). In another variation, the retention mechanism 110 defines a first edge and a second edge opposing the first edge, and includes a set of appendages 117 that extend away from the first edge and are configured to couple to the second edge (e.g., removably couple via buckles, hook-and-loop-fasteners, etc.) such that the retention mechanism no can be wrapped (e.g., secured) around the body region of the user and compress the body region of the user. In another variation, the retention mechanism 110 is configured to self-retain at a musculoskeletal or other body region of a user 900 by inherent elasticity; for example, the retention mechanism no can include a tubular sleeve that is comprised of an elastic material, wherein the retention mechanism no can be slid over the knee region of a user and maintains its position at the knee region through friction, the friction generated by an inward radial force supplied by the elastic material of the tubular sleeve. However, the retention mechanism 110 can have any other suitable geometry.

The system preferably includes a single retention mechanism no (e.g., sleeve) that retains all of the temperature modulation subsystems. However, the retention mechanism 110 can additionally or alternatively be segmented and/or separable into distinct independently positionable retention mechanisms, each retention mechanism 110 configured to retain one or more temperature modulation subsystems adjacent to a body region of a user 900 (e.g., as in an elbow sleeve including a series of multiple armbands, each armband having a substantially similar structure and interchangeable with others of the series of armbands). However, the system can include any suitable number of retention mechanisms.

Figure 9:
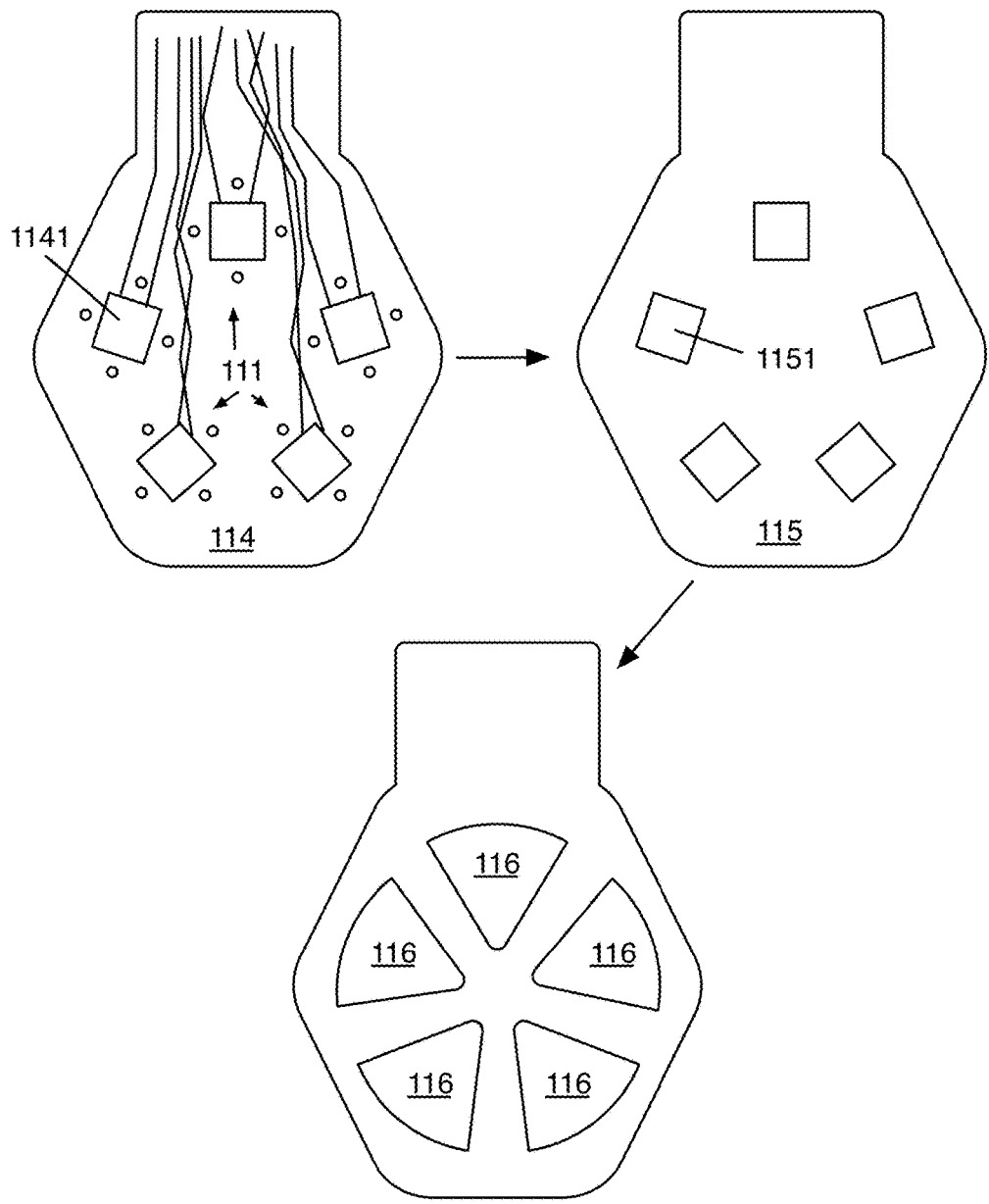
FIG. 9 is a top view of a sequence of layers and electrical conduit routing between the sequence of layers in an example embodiment of the system.
Figure 11:
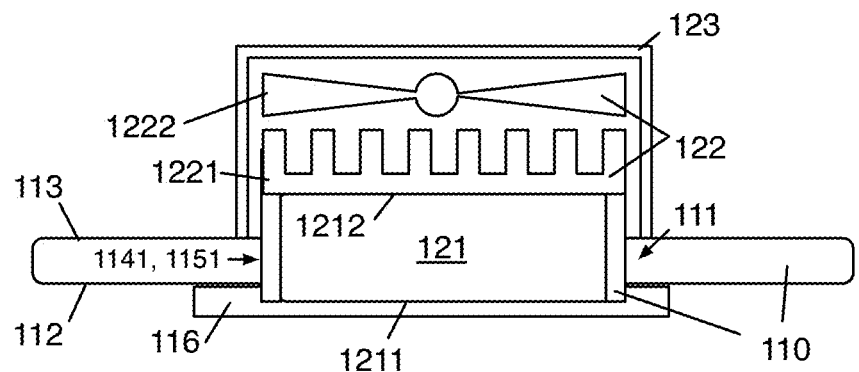
FIG. 11 is a cross sectional view of a variation of the temperature modulation subsystem coupled to a variation of the retention mechanism.

The retention region 111 (e.g., coupling interface) of the retention mechanism 110 functions to retain the temperature modulation subsystem 120 adjacent to a body region of the user. A retention region 111 can, in variations, include an electromechanical coupler, a pocket, a sleeve, a set of layers, a hole or aperture pattern, and/or define or include any suitable mechanical feature for retaining a temperature modulation subsystem. In a first variation, the temperature modulation subsystems are integrated into the retention mechanism 110 at the retention region. For example, a portion of the retention mechanism 110 is sewn around a portion of the temperature modulation subsystem, in order to integrate the temperature modulation subsystem 120 into the retention mechanism 110 and arrange the temperature modulation subsystem 120 adjacent to the user. In a second variation, the retention region 111 includes a receiving surface that mates to a corresponding surface of the temperature modulation subsystem. The receiving surface can be a male surface feature, wherein the corresponding surface feature of the temperature modulation subsystem 120 is female. The receiving surface can be a female surface feature, wherein the corresponding surface feature of the temperature modulation subsystem 120 is male. In alternatives, the receiving region can include both male and female surface features, wherein the temperature modulation subsystem 120 includes mating surface features, a threaded interface (e.g., male, female), and/or any other suitable mechanism for securely coupling to and retaining the temperature modulation subsystem. In a third variation, the retention region 111 defines an aperture that receives a portion of the temperature modulation subsystem 120 and a hole pattern 1111 that receives a corresponding set of fasteners configured to couple the temperature modulation subsystem 120 around a layer of the retention mechanism, as shown in FIGS. 9 and 11. However, the retention region 111 can be otherwise suitably configured.

In a first example, the retention mechanism 110 includes a first, second and third layer 116 in a stacked configuration. The first layer 114 defines a first aperture 1141 (e.g., a hole) adapted to receive a portion of the temperature modulation subsystem, and the second layer 115 defines a second aperture 1151 likewise adapted to receive the portion of the temperature modulation system and aligned with the first aperture 1141 (e.g., identically overlapping, concentrically arranged, etc.). Thus, in this example, the apertures of the first and second layers define the retention region 111 of the retention mechanism. The third layer 116 in this example does not include an aperture, and acts as a barrier between the portion of the temperature modulation subsystem 120 which extends through the apertures of the first and second layer 115 and the body region (e.g., skin at the body region) of the user. However, in other examples, the third layer 116 can include an aperture configured to expose the portion of the temperature modulation subsystem 120 to the body region of the user and/or be otherwise suitably configured. In this example, electrical conduits (e.g., power wires, control wires, etc.) are routed between the first and second layers such that the wires are not exposed at either an external side 113 (e.g., outermost side) of the retention mechanism 110 or an internal side 112 (e.g., innermost side) of the retention mechanism. However, in other examples, electrical conduits can be otherwise suitably routed amongst layers of the retention mechanism 110 (e.g., electrical conduits can include conductive thread integrated into the retention mechanism). In this example and related examples wherein the retention mechanism 110 includes a plurality of layers, the layers are preferably sewn together, and preferably sewn together such that the temperature modulation subsystem 120 is at least partially captured between two or more layers in order to retain the temperature modulation subsystem. However, in such examples, the temperature modulation subsystem 120 can be otherwise suitably coupled to the layer(s) of the retention mechanism 110 (e.g., via threaded fasteners, rivets, clips, etc.).

3.2—Temperature Modulation Subsystem

Figure 3:
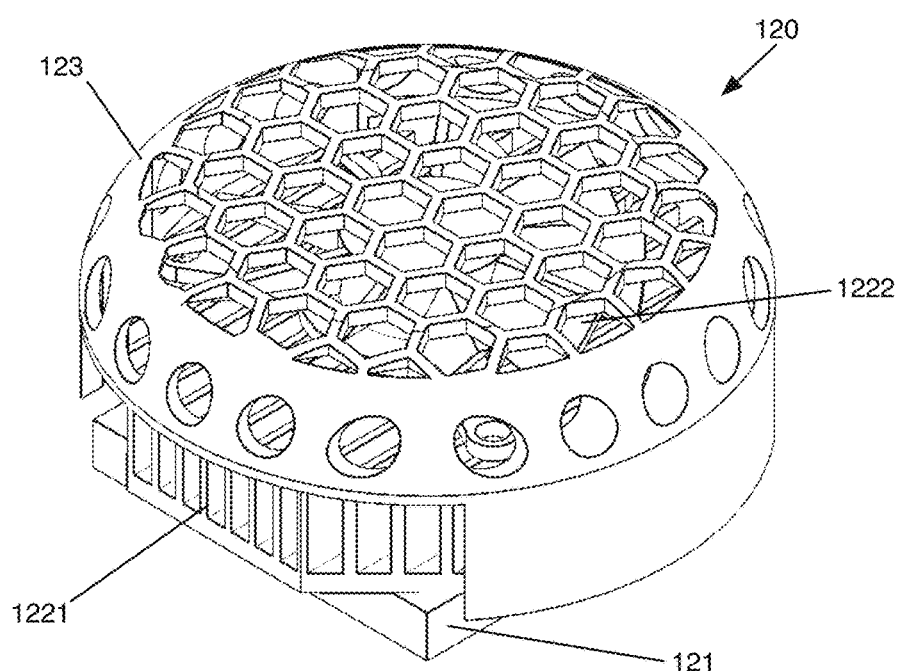
FIG. 3 is a perspective view of a variation of the temperature modulation subsystem of the system.

The temperature modulation subsystem 120 functions to provide an interfacial surface (e.g., between the system and the user) having a controllable temperature. The temperature modulation subsystem 120 can also function to provide a surface that can be placed against a skin region of the user in an area where the user desires hot and/or cold therapy. As shown in FIG. 3, the temperature modulation subsystem 120 includes a temperature controllable layer 121 (e.g., temperature-controllable substrate), a heat exchanger 122, and a shield 123. The heat exchanger 122 preferably includes an active heat transfer element 1222 and a passive heat transfer element, but can alternatively include either an active heat transfer element 1222 or a passive heat transfer element. The temperature modulation subsystem 120 can optionally include a connector that supports electrical coupling (e.g., to a power management system, to a data link, etc.). Each instance (e.g., unit) of the temperature modulation subsystem 120 (e.g., in variations including a plurality of temperature modulation subsystems) is preferably connected to the power supply module 140 (e.g., by a direct electrical connection configured to supply electrical power), to the control module 130 (e.g., by a data connection configured to send and receive data, a wired connection, a wireless connection, etc.), and physically coupled to and retained by the retention mechanism no (e.g., at the retention region of the retention mechanism). In some variations, the power and/or data connections can be removable (e.g., via an electromechanical coupler). Connections can also be routed through the retention mechanism no (e.g., between fabric layers of the retention mechanism, integrated into conductive thread of the retention mechanism, etc.). Furthermore, connections can additionally or alternatively be sealed within the retention mechanism no (e.g., between layers of the retention mechanism) using materials that provide a waterproof boundary that fully encloses the electrical connections (e.g., to avoid electrical shorting when the retention mechanism is in contact with water, sweat, and/or other liquids).

Figure 7A:
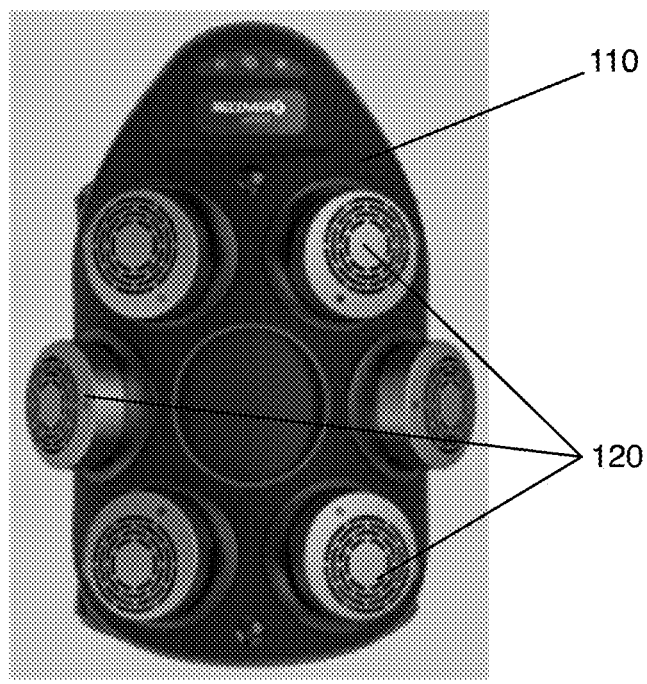
FIG. 7A is a frontal view of a specific example embodiment of the system.

In variations, the system includes a plurality of temperature modulation subsystems, arranged in a predetermined pattern (e.g., defined by a pattern of retention regions at the retention mechanisms). In a specific example, as shown in FIGS. 7A and 7C, the system includes six temperature modulation subsystems arranged in a substantially hexagonal array proximal the edges of an ovoid broad surface of the retention mechanism. However, the system can additionally or alternatively include any suitable number of temperature modulation subsystems, arranged in any suitable manner (e.g., including modular, reconfigurable temperature modulation subsystems). As such, in some variations, multiple temperature modulation subsystems can be repositioned relative to the retention mechanism 110 by the user or another entity, in order to provide a customizable configuration of the system (e.g., for use on various body regions of the user in different customized configurations).

Figure 6A:
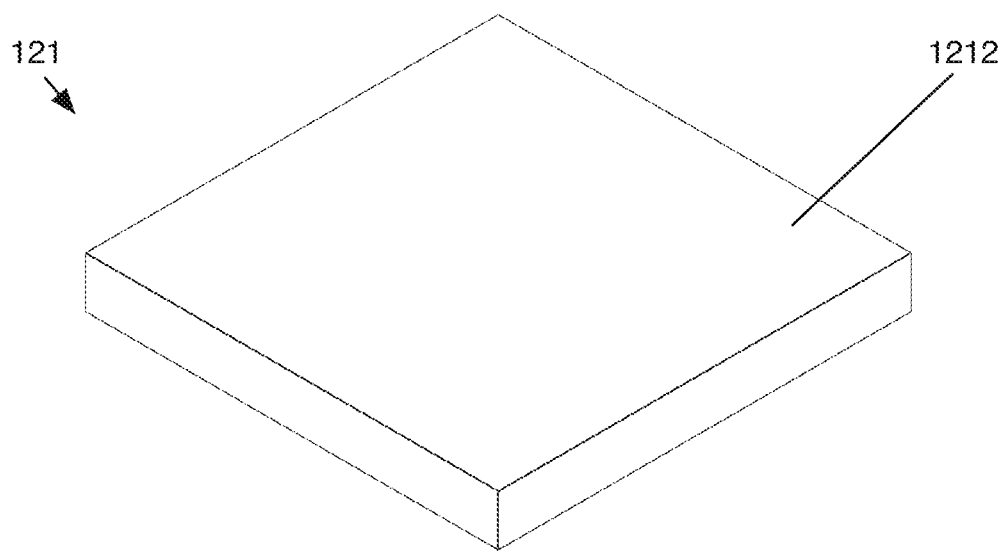
FIG. 6A is a perspective view of a variation of the temperature controllable layer of the temperature modulation subsystem.
Figure 6B:
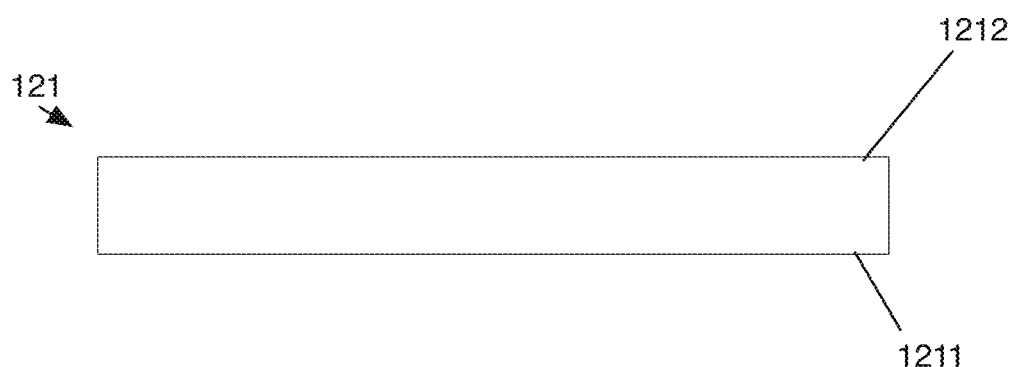
FIG. 6B is a side view of the variation of the temperature controllable layer of the temperature modulation subsystem depicted in FIG. 6A.

The temperature controllable layer 121 functions to provide a thermomechanical interface through which heat is exchanged with a user at a skin region. The temperature controllable layer 121 can optionally include an interface layer (e.g., a thermal pad, a gel layer, etc.). As shown in FIGS. 6A-B, the temperature controllable layer 121 preferably defines a contact surface (e.g., proximal surface) that functions as the actively heated and/or cooled surface of the temperature controllable layer 121 that is maintained at a set temperature (e.g., set by the control module, set by the user at a client application in communication with the control module, etc.). The contact surface can have any suitable shape, but is preferably a broad surface. The temperature controllable layer 121 also preferably defines a non-contact surface (e.g., distal surface) that functions as the surface at which waste heat is rejected and/or from which heat is extracted (e.g., in cases wherein the contact surface is being heated and/or the temperature modulation system is operated in the heating mode). The temperature controllable layer 121 is preferably in contact with a temperature sensor 132, to enable automatic closed-loop control of the temperature of the contact surface in cooperation with the control module 130 and/or other controller (e.g., a client application executing on a mobile device).

The temperature controllable layer 121 can optionally include an interface layer (e.g., a resilient interface layer) that functions to provide a conforming material layer between the contact surface and a skin region of the user (e.g., to enhance user comfort, to enhance heat transfer, etc.). In a specific example, the interface layer includes a thermal pad, wherein the thermal pad extends over an area of the internal surface of the retention mechanism 110 that substantially corresponds to the projected area of the temperature controllable layer 121 and does not extend substantially beyond the projected area of the temperature controllable layer. In another example, the interface layer can include a gel layer (e.g., a liquid gel, a semi-liquid gel, a solidified gel, etc.). In another example, the interface layer can include a layer of the retention mechanism 110 (e.g., the third layer) and can be fabricated from a thermally-conductive material (e.g., a material having a higher thermal conductivity than cotton, silk, nylon, acrylic, and other natural and man-made fabrics). In further examples, the interface layer can include a plurality of sub-layers including any of the aforementioned example interface layer types and/or any other suitable layers or materials (e.g., a plastic liner having any suitable thermal properties), in order to improve device flexibility when coupling the device to a user. However, the temperature controllable layer 121 can otherwise include and/or define any suitable components.

The temperature controllable layer 121 is preferably arranged as the system component most proximal the user in order to facilitate efficient heat transfer to and/or from the skin region of the user. The temperature controllable layer 121 (e.g., the non-contact surface of the temperature controllable layer) is preferably in thermal contact with the passive heat transfer element. However, the temperature controllable layer 121 can be otherwise suitably arranged.

In a first variation, the temperature controllable layer 121 is a thermoelectric cooling and/or heating device (e.g., a Peltier cooler and/or heater, any other suitable type of thermoelectric cooler/heater or panel, etc.), wherein an applied voltage generates a temperature differential between the contact and non-contact surface that is based on the applied voltage. In a specific example of the first variation, the temperature controllable layer 121 includes a Peltier thermoelectric module defining a rectilinear cross section (e.g., 40 mm×40 mm, any other suitable footprint) and having a defined thickness (e.g., 4.2 mm, any other suitable thickness), and adapted to receive a range of currents (e.g., between 0.5-2 A) at a specified voltage (e.g., approximately 15 V) that can be reversed in polarity in order to generate either a high temperature (e.g., 100-120° F.) or a low temperature (e.g., 40-60° F.) at the contact surface. However, in this variation, the thermoelectric panel can additionally or alternatively be otherwise suitably configured.

In a second variation, the temperature controllable layer 121 defines an internal void (e.g., a hollow interior of the layer, a set of tubes, etc.) through which a circulating fluid is pumped through the temperature controllable layer 121 by a pumping mechanism of the temperature control subsystem, wherein the circulating fluid is heated and/or cooled to a controlled temperature (e.g., a high temperature, a low temperature, etc.).

The heat exchanger 122 functions to transport energy (e.g., in the form of heat) from the distal surface of the temperature controllable layer 121 (e.g., the side of the layer opposite the user-adjacent side) to the ambient environment surrounding the system. The heat exchanger 122 preferably includes a passive heat transfer element 1221 and an active heat transfer element. However, the heat exchanger 122 can additionally or alternatively include any other suitable components for exchanging energy between the temperature modulation subsystem and the ambient environment.

Figure 5A:
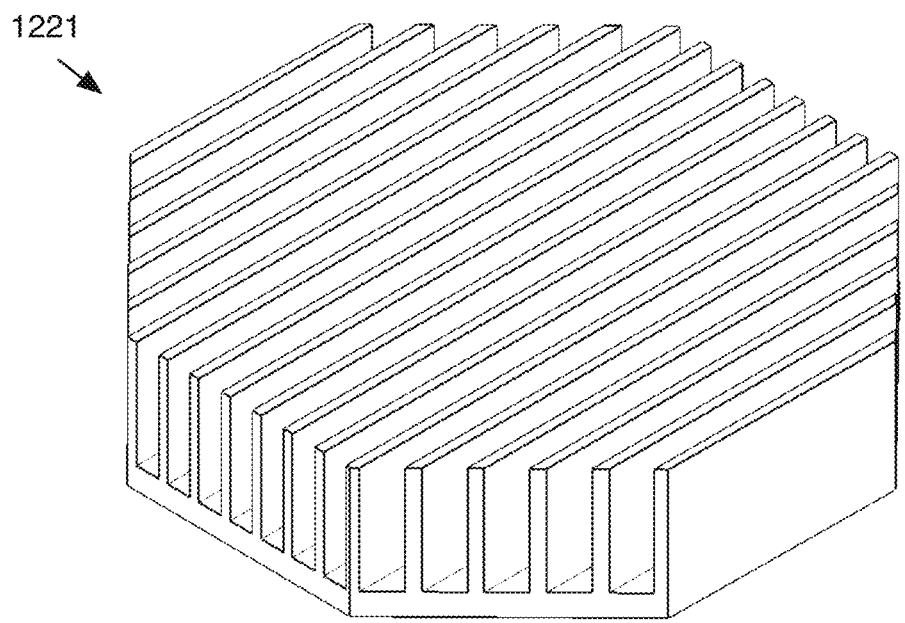
FIG. 5A is a perspective view of a variation of a passive heat transfer element of the temperature modulation subsystem.
Figure 5B:
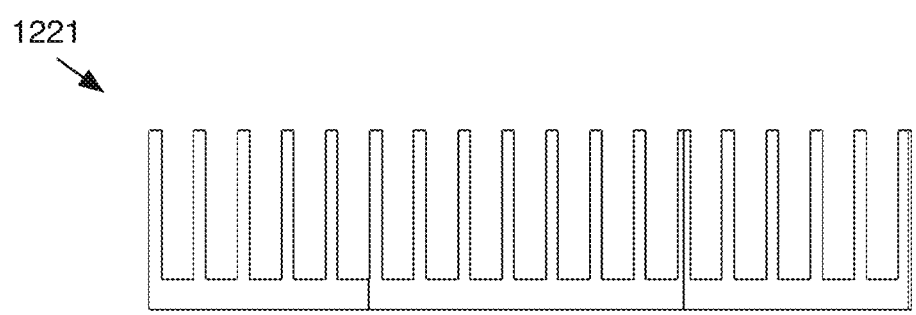
FIG. 5B is a side view of the variation of the passive heat transfer element of the temperature modulation subsystem depicted in FIG. 5A.

The passive heat transfer element 1221 functions to dissipate heat that is exchanged with the user through the temperature controllable layer. The passive heat transfer element 1221 is preferably a heat sink, but can additionally or alternatively include any other suitable heat transfer element. As shown in FIGS. 5A-B, the passive heat transfer element 1221 preferably defines a surface (e.g., a broad surface) in thermal contact with the non-contact surface of the temperature controllable layer. The passive heat transfer element 1221 can optionally include portions that are thermally and mechanically contiguous with the above surface that extend away from the surface (e.g., fins, posts, etc.) that are configured to increase the thermal mass of portions of the passive heat transfer element 1221 distal the non-contact surface, and to increase the surface area of the passive heat transfer element 1221 (e.g., to maximize available surface area available for conductive and/or convective heat transfer away from the passive heat transfer element).

In a first variation, the passive heat transfer element 1221 defines a broad surface in thermal and physical contact with the non-contact surface of the temperature controllable layer. In a specific example, the broad surface has a substantially hexagonal footprint as shown in FIG. 5A, but in alternative examples can have any suitable footprint and/or shape. In a second variation, the passive heat transfer element 1221 defines a set of fins extending (e.g., perpendicularly) away from the broad surface. The fins can have any suitable thickness, extent, and/or other suitable properties (e.g., in order to maximize surface area and/or heat transfer properties). In a third variation, the passive heat transfer element 1221 defines a block of thermally conductive material and defines one or more internal lumens through which fluid can be passed to enhance heat transfer away from surfaces of the block.

The passive heat transfer element 1221 is preferably made up of a material having a high thermal conductivity (e.g., aluminum, copper, etc.), but can additionally or alternatively include any suitable material. In some variations, the passive heat transfer element 1221 includes a phase-changing material (e.g., enclosed within the passive heat transfer element) that can absorb and/or reject heat as it changes phase, in order to increase the rate of heat transfer from the surfaces of the passive heat transfer element 1221 and store energy in the chemical bonds of the phase-changing material. However, the passive heat transfer element 1221 can otherwise include any suitable materials for any suitable purpose.

The active heat transfer element 1222 functions to promote convective activity proximal the passive heat transfer element 1221 to increase convective heat transfer to and/or from the passive heat transfer element. The active heat transfer element 1222 is preferably a fan (e.g., a rotary fan), but can additionally or alternatively include any suitable active heat transfer element 1222 (e.g., a circulating-fluid heat exchanger, an evaporative heat exchanger, a condenser, a refrigerator, etc.). The active heat transfer element 1222 is preferably physically coupled to a motor that functions to rotate the active heat transfer element 1222 (e.g., the fan blades) and thereby actively convect fluid towards and/or away from the passive heat transfer element. In a first variation, the motor includes thermally-conductive elements (e.g., a housing, thermally conductive feedthroughs, etc.) that are thermally coupled to the passive heat transfer element 1221 and/or other components of the temperature modulation subsystem. In another variation, the motor includes fins that extend away (e.g., radially) from the housing of the motor and can function to aid heat transfer away from the motor during operation and/or from the passive heat transfer element 1221 (e.g., to aid heat transfer away from the non-contact surface of the temperature controllable layer).

In a first variation, as shown in FIG. 3, the active heat transfer element 1222 includes a fan, arranged between the passive heat transfer element 1221 (e.g., heat sink) and the shield 123, defining an axis of rotation perpendicular to the broad surface of the passive heat transfer element, and having a footprint (e.g., projected area) that extends substantially completely over a projected area of the broad surface. In some examples, the footprint of the passive heat transfer element 1221 can be substantially identical to the footprint of the fan (e.g., a circular footprint of the same dimensions) and aligned therewith. In alternative examples, the footprints of the passive heat transfer element 1221 and the fan can be dissimilar, and relatively aligned in any suitable manner.

Figure 10:
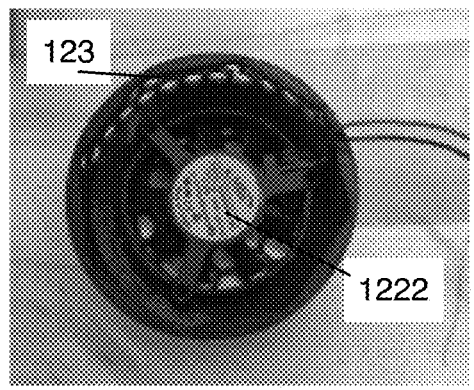
FIG. 10 is a perspective view of an internal arrangement of a portion of an example embodiment of the temperature modulation subsystem.

The fan is preferably attached directly to the shield 123, such that the shield 123 acts as the only barrier between the fan blades and the external environment (e.g., the fan preferably does not include an additional protective housing besides the shield). In an example, the fan is attached directly to the shield 123 by way of three equally spaced threaded fasteners, which correspond to three equally spaced threaded orifices located at an inner rim of the shield 123 (e.g., as shown in FIG. 10). The fan is preferably configured to maximize airflow through the temperature modulation subsystem 120 (e.g., the heat sink) while minimizing the thickness of the fan in the direction perpendicular to the body region of the user. Accordingly, the fan can include a number of fan blades (e.g., six, eight, nine, ten, etc.) which have a large aspect ratio (e.g., are long and comparatively thin), in order to reduce the thickness of the fan. In a specific example, as shown in FIG. 10, the fan includes nine blades attached to a hub, and the hub includes three members that extend radially from the central axis of the fan towards the shield 123. The three members are attached to the shield 123 by way of threaded fasteners such that the fan is arranged in a recessed portion of the shield cavity 1231 proximal the set of apertures. Additionally or alternatively, the fan can have any suitable number of blades having any suitable aspect ratio.

Figure 12:
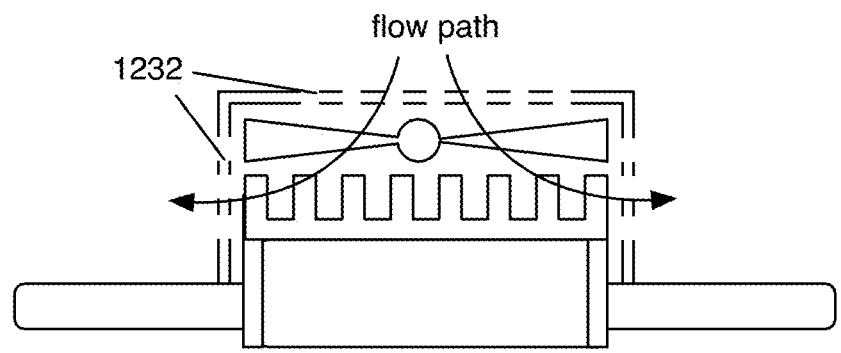
FIG. 12 is a cross sectional view of a variation of the temperature modulation subsystem depicting an example flow path through the temperature modulation subsystem.

The fan can be configured to generate any suitable airflow path through the shield cavity 1231, in order to transfer energy between the passive heat transfer element 1221 and the ambient environment. An example flow path, as shown in FIG. 12, can include drawing air inward through the set of apertures at a top region of the shield 123 and expelling air from the set of apertures at side regions of the shield 123. However, the fan can additionally or alternatively generate any suitable flow path.

In a second variation, the active heat transfer element 1222 is arranged within a housing and pumps fluid through an inlet port and an outlet port defined by the housing. In this variation, the system includes multiple temperature modulation subsystems, and fluid flow between the inlet and outlet port of each temperature modulation subsystem 120 is driven by a reduced number of active heat transfer elements (e.g., such that there are fewer fans than temperature modulation subsystems). In this variation, portions of the active heat transfer element 1222 of each temperature modulation subsystem 120 are connected together into a fluid-flow manifold. However, in these and other variations, the active heat transfer element 1222 can be otherwise assembled in any suitable manner.

Figure 4A:
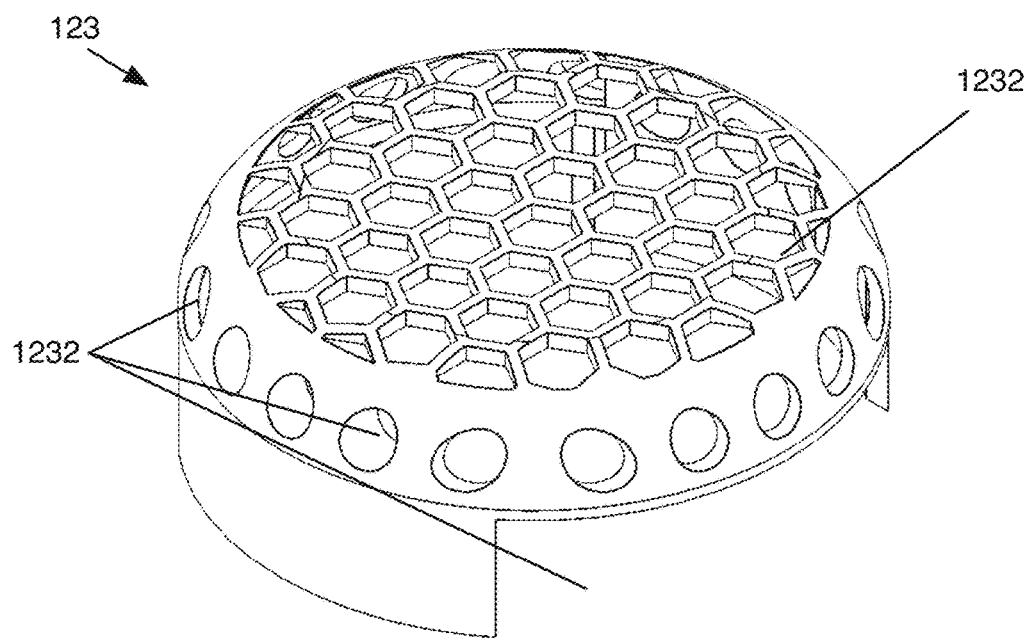
FIG. 4A is a perspective view of a variation of a shield of the temperature modulation subsystem.
Figure 4B:
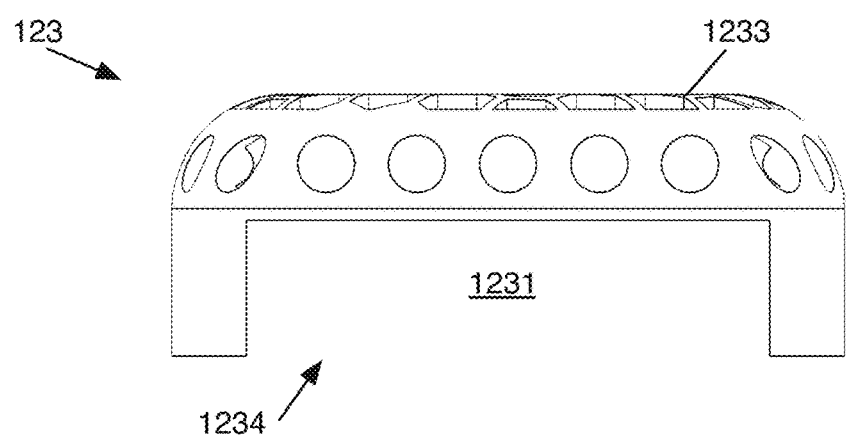
FIG. 4B is a side view of the variation of the shield of the temperature modulation subsystem depicted in FIG. 4A.
Figure 13:
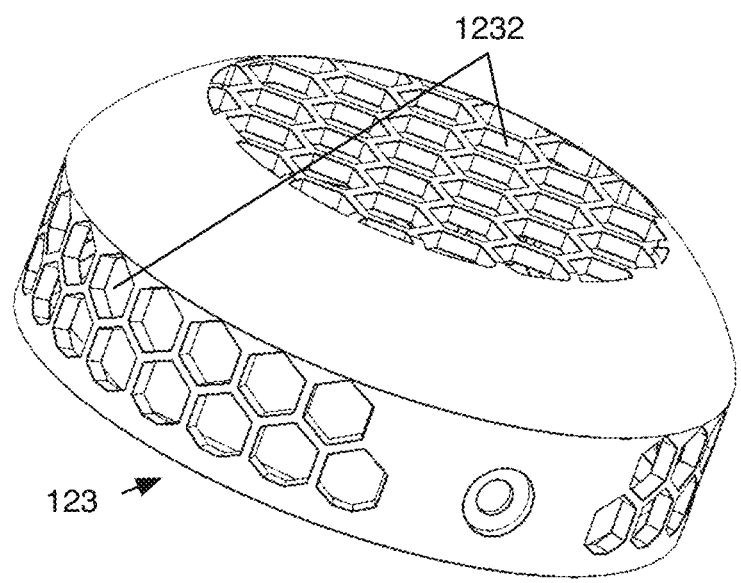
FIG. 13 is a perspective view of a variation of the shield of the temperature modulation subsystem.

The shield 123 functions to prevent mechanical interference with the active heat transfer element 1222 while promoting efficient fluid flow to and/or from the active and passive heat transfer elements. The shield 123 can also function to protect the user. As shown in FIGS. 4A-B and 13, the shield 123 preferably defines apertures that function to enable fluid flow between the external environment (e.g., air) and the passive heat transfer element, driven and/or moderated by the active heat transfer element 1222 (e.g., fan) and/or natural convection (e.g., in cases wherein the active heat transfer element 1222 is in an inactive state). The shield 123 also preferably defines a lumen that functions to house the active heat transfer element. However, the shield 123 can additionally or alternatively include and/or define any suitable components and/or features.

The shield 123 is preferably rigidly coupled to the passive heat transfer element, but can be otherwise suitably coupled to other suitable components of the system. The shield 123 can, in variations, be composed of material with thermal properties to promote heat transfer (e.g., high thermal conductivity materials), but can additionally or alternatively be composed of any suitable materials.

In a specific example, as shown in FIGS. 4A and 4B, the shield 123 defines a substantially cylindrical lumen having an open end 1234 and a closed end 1233, wherein the open end 1234 is arranged to receive a surface of the passive heat transfer element 1221 and the closed end 1233 is arranged distal the user of the system (e.g., most distal the contact surface of the temperature controlled layer). In this example, the active heat transfer element 1222 (e.g., a fan) is arranged within the cylindrical lumen and can freely rotate, and the shield 123 further defines a set of apertures arranged at the closed end 1233 in a hexagonal close-packed array. The apertures can have any suitable shape and/or profile (e.g., circular, hexagonal, pentagonal, etc.). In this example, the set of apertures in the close-packed array extend substantially over the entirety of the closed end 1233 of the shield 123. In this specific example, the sides of the shield 123 are formed by a set of pillars that collectively stand the closed end 1233 off from the passive heat transfer element 1221 and cooperatively define the shield cavity 1231 along with the closed end 1233. The set of pillars in this example are preferably spaced apart such that airflow is permitted between each of the set of pillars (e.g., airflow actively driven by a fan within the shield cavity).

In a related specific example, as shown in FIG. 13, the set of apertures of the shield 123 are arranged in a close-packed array that extends substantially over the closed end 1233 and the sides of the shield 123.

The connector functions to provide electrical power to the temperature modulation subsystem. The connector can also function to provide control signals to the temperature modulation subsystem 120 (E.g., to control the temperature of the temperature controllable layer). The connector can also function to transmit output data (e.g., data corresponding to the temperature of the contact surface that is collected by the temperature sensor) from the temperature modulation subsystem 120 (e.g., to the control module).

The connector is preferably physically connected to the power supply module 140 (e.g., via direct electrical connection) and the control module 130 (e.g., via direct electrical connection, wireless connection, etc.). In variations in which the temperature modulation subsystem 120 is modular (e.g., removable), the connector can likewise be removable (e.g., as an electromechanical port) such that the temperature modulation subsystem 120 can be removed from the retention region 111 of the retention mechanism no (e.g., to facilitate repositioning of the temperature modulation subsystem, washing of the retention mechanism, etc.). The connector can have any suitable geometry (e.g., male, female, a combination of male and female, threaded, etc.), and be any suitable type of connector (e.g., a barrel connector, a USB connector, etc.). The temperature modulation subsystem 120 preferably includes a single integrated connector that functions to transfer power and data, but can additionally or alternatively include any suitable number of connectors having any suitable purpose (e.g., dedicated connectors for power and data separately).

3.3—Control Module

The control module 130 functions to determine control instructions, and to control the temperature modulation subsystems according to the determined control instructions. The control module 130 can also function to receive control instructions and/or generate control instructions (e.g., at a mobile device platform or application, an integrated user interface, etc.). The control module 130 can also function to apply a control voltage to the temperature modulation subsystem 120 such that a desired temperature (e.g., a high temperature, a low temperature, etc.) is generated at the contact surface of the temperature modulation subsystem 120 and thereby at the body region of the user. The control module 130 includes a processor, and can optionally include a communications module. The control module 130 is preferably communicatively coupled to each temperature modulation subsystem 120 (e.g., via physical data connection, a wireless data connections such as Bluetooth, etc.), and can optionally be communicatively coupled to a mobile device 910 of the user (e.g., via a Wi-Fi radio, Bluetooth, Bluetooth low-energy/BLE, any other suitable wireless communication protocol, a wired connection, etc.). As such, in specific applications, the control module 130 can be at least partially executable through a mobile application platform of a mobile device 910 of the user. In a first variation, the system includes a single control module 130 simultaneously coupled to each temperature modulation subsystem 120 of the system. In a second variation, each temperature modulation subsystem 120 is coupled to a corresponding control module 130. However, alternative variations can have any suitable correspondence between any number of control module 130s and temperature modulation subsystems. The control module 130 is preferably retained by the retention mechanism 110 (e.g., sewn into the retention mechanism, coupled via a male/female interface, removably coupled and retained by a sleeve, etc.), but can additionally or alternatively be remote, removed, and/or separate from the retention mechanism 110 (e.g., coupleable via a removable connector, a wireless communication link, etc.). However, the control module 130 can be otherwise suitably arranged and/or located.

The control module 130 can include a temperature sensor 132 that functions to monitor the temperature of the contact surface of the temperature controllable layer 121. The output of the temperature sensor 132 (e.g., an analog or digital signal indicative of the temperature of the contact surface) is preferably provided to the control module 130 via a direct data connection (e.g., a serial bus, a double-ended signal-transmission wire pair, etc.), but can be otherwise suitably coupled. The control module 130 preferably includes a temperature sensor 132 corresponding to each temperature modulation subsystem 120, but can additionally or alternatively include any suitable number of temperature sensors relative to the number of temperature modulation subsystems (e.g., multiple temperature sensors per temperature modulation subsystem, a single temperature sensor arranged amid multiple temperature modulation subsystems, etc.). The temperature sensor can include any suitable type of temperature sensor, such contact sensors (e.g., thermocouples, thermistors, digital thermometers, analog thermometers, etc.) and non-contact sensors (e.g., infrared thermometers, radiative temperature sensors, scattered emission thermometers, etc.). The temperature sensor can be arranged adjacent to (e.g., touching) the contact surface, proximal the contact surface (e.g., retained by the retention mechanism within 1 mm, 2 mm, or any other suitable distance relative to the contact surface), adjacent to (e.g., touching) the non-contact surface, proximal the non-contact surface, and at any other suitable position relative to the surface(s) of the temperature controllable layer. In a specific example, the temperature sensor is flush-mounted with the contact surface of the temperature controllable layer. However, the temperature sensor can additionally or alternatively be otherwise suitably arranged.

Figure 7B:
FIG. 7B is a perspective view of a portion of the specific example embodiment of the system depicted in FIG. 7A.
Figure 7C:
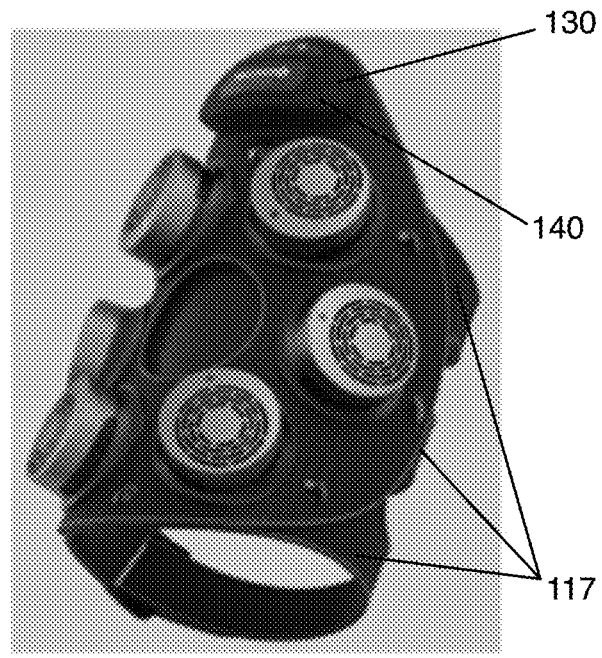
FIG. 7C is a perspective view of the specific example embodiment of the system depicted in FIG. 7A.
Figure 8:
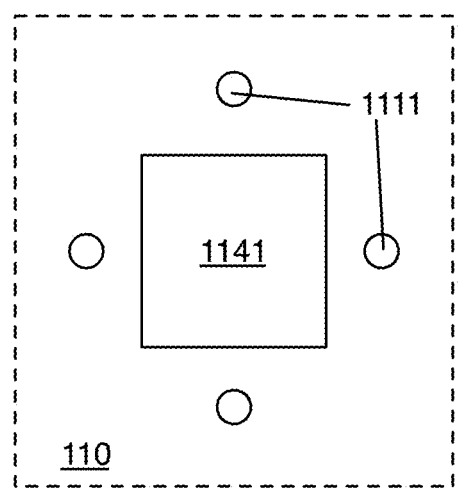
FIG. 8 is a top view of an example hole pattern and aperture in a layer of a variation of the retention mechanism.

As shown in FIG. 7B, the control module 130 can include user inputs 133 that are arranged on the outside of the retention mechanism no (e.g., so as to be accessible to a user). Such user inputs 133 can include a power button (e.g., to turn the system into an 'on' state and/or 'off' state), a therapy-type-selector button (e.g., a cold button, a hot button, etc.), and any other suitable input mechanisms. Additionally or alternatively, user inputs 133 can be provided via a wireless link (e.g., from a client application executing at a mobile device of the user). In some variations, the system can omit user input mechanisms arranged at the retention mechanism 110 and be controllable solely by way of a separate remote controller (e.g., a dedicated remote controller, a client application on a remote computing system, etc.) in wireless communication with the control module 130.

3.4—Power Supply Module

The system can include a power supply module 140, which functions to provide electrical power to the temperature modulation subsystem 120 and the control module 130. The power supply module 140 can also function to store energy to provide portable functionality (e.g., portability) to the system. The power supply module 140 can include a battery, power regulation circuitry, a charging interface, and any other suitable components for power supply and storage. The power supply module 140 is preferably coupled to the control module 130 (e.g., via direct electrical connection, an electrical cable, conductive stitching integrated into the retention mechanism, etc.) in a manner that promotes efficient routing relative to the retention mechanism, the temperature modulation subsystem 120 (e.g., to provide power via a direct electrical connection), and is preferably coupleable (e.g., via the charging interface) to a source of grid power (e.g., alternating current, regulated direct-current, wall power, etc.). However, the power supply module 140 can be otherwise suitably coupled to other system components in any suitable manner.

3.5—Additional System Elements

The system can optionally include additional sensors, such as pressure sensors, blood flow sensors (e.g., ultrasound acoustic flow sensors, optical sensors), heart rate sensors, blood pressure sensors, and/or any other suitable sensors that can detect any suitable biometric characteristic. For instance, processing of information from such sensors can be used to determine characteristics related to physiological inflammation proximal the device position, and to provide a feedback mechanism for operation of the system in relation to the provided heat/cold therapy. Additional sensors are preferably powered by (e.g., connected to by an electrical connection) the power supply module 140, but can be otherwise suitable powered (e.g., by a dedicated battery, energy harvesting from the user via a thermoelectric generator, a mechanical energy harvester, etc.). Additional sensors are preferably integrated into the temperature modulation subsystems and can be arranged adjacent to the user (e.g., embedded in the contact layer and/or interface layer of the temperature controllable layer, outside the footprint of the contact layer, etc.) or otherwise suitably arranged. Additional sensors are preferably retained by the retention mechanism, but can be otherwise suitably retained (e.g., by a separate mechanism such as a heart rate monitor strap).

The system can optionally include specialized therapy provision modules, in addition to the temperature modulation subsystem, retained at the body region of the user by the retention mechanism. The specialized therapy provision modules function to enable therapeutic treatments of the body region of the user in addition to and/or instead of hot and cold therapies. In one variation, the specialized therapy provision modules include a transcutaneous electrical nerve stimulation (TENS) subsystem. The TENS subsystem functions to provide direct current stimulation to the body region of the user and thereby therapeutically interact with the user (e.g., relieve pain of the user, relax musculature of the user, etc.). The TENS subsystem can be integrated into the temperature modulation subsystem, such that the contact surface is in electrical contact with the body region of the user (e.g., to enable the delivery of electrical stimulation by way of direct electrical current, alternating current, etc.). Alternatively, the TENS subsystem can be distinct from the temperature modulation subsystem.

In another variation, the specialized therapy provision modules include an active compression subsystem. The active compression subsystem functions to compress the body region of the user, and can function to do so in a controllable manner (e.g., to provide a controllable compression pressure). In one example, the active compression subsystem includes a pressurizable bladder integrated into the retention mechanism, and can be controllably filled with a pressurized fluid having a selected pressure in order to compress the body region of the user. In another example, the active compression subsystem includes an electro-active polymer integrated into the retention mechanism, and can be electrically activated to contract around the body region of the user and thereby compress the body region of the user. In yet another example, the active compression system includes a ratchet that attaches the set of appendages at the second edge of the retention mechanism, and the ratchet can be actuated (e.g., by the controller) to tighten the set of appendages around the body region of the user and thereby compress the body region.

However, the specialized therapy provision modules can additionally or alternatively include suitable components for the provision of any suitable therapies.

3.6—Specific Examples

In a first specific example, the wearable personal cooling and heating system for placement at a body region of a user 900 includes a retention mechanism, a temperature modulation subsystem, and a control module 130. The retention mechanism 110 includes a first layer 114 defining a first aperture, a second layer 115 defining a second aperture 1151 aligned with the first aperture, and a third layer 116 fabricated from a thermally-conductive fabric. The third layer 116 is arranged adjacent to the body region of the user, and the first, second, and third layers are arranged in a stacked configuration. The temperature modulation subsystem 120 includes a thermoelectric panel that defines a first side and a second side opposing the first side, a heat sink in direct contact with the thermoelectric panel at the second side, a fan arranged proximal to the heat sink, and a shield 123 attached to the thermoelectric panel that defines a shield cavity 1231 that contains the heat sink and the fan. The thermoelectric panel extends through the first and second apertures of the retention mechanism, and is in thermal contact with the third layer 116 of the retention mechanism 110 at the first side, as shown by example in FIG. 11. The shield 123 also defines an external surface in which are defined a set of airflow apertures 1232. The fan is configured to actively drive airflow through the set of airflow apertures 1232 and along a flow path adjacent to the heat sink. The control module 130 is retained by the retention mechanism 110 and is communicatively coupled to the temperature modulation subsystem 120 by way of a direct electrical connection routed between the first and second layers of the retention mechanism. The control module 130 is also configured to operate the temperature modulation subsystem, which is operable between a cooling mode and a heating mode by the control module 130. The cooling mode includes powering the thermoelectric panel with a first applied voltage having a first polarity and thereby generating a low temperature at the first side of the thermoelectric panel, and the heating mode includes powering the thermoelectric panel with a second applied voltage having a second polarity opposite the first polarity and thereby generating a high temperature at the first side of the thermoelectric panel.

In a related example, the retention mechanism no defines a first edge and a second edge opposing the first edge, and also includes a set of appendages 117 that extend away from the first edge as shown in FIG. 2. The set of appendages 117, in this example, can removably couple to the retention mechanism no at regions proximal to the second edge (e.g., as shown in FIG. 7C) and thereby secure the retention mechanism no in a first configuration at the body region of the user. In the first configuration, the retention mechanism 110 compresses the body region of the user and arranges the temperature modulation subsystem 120 at the body region of the user. In another related example, the system includes a plurality of temperature modulation subsystems attached to the retention mechanism 110 and which are arranged in a hexagonal array, wherein, in the first configuration, the hexagonal array surrounds a joint region of the user.

In another related example, the system includes a temperature sensor 132 in direct thermal contact with the temperature-controllable substrate and communicatively coupled to the control module 130, wherein the cooling mode comprises maintaining the low temperature based on an output of the temperature sensor 132, and wherein the heating mode comprises maintaining the high temperature based on the output of the temperature sensor 132.

In another related example, the control module 130 is communicatively coupled to (e.g., in wireless communication with) a client application 131 executing on a mobile device 910 associated with the user. In this example, the temperature modulation subsystem 120 is operable between the cooling mode and the heating mode based on instructions received from the user by way of the client application 131.

The systems and methods of the preferred embodiment and variations and examples thereof can be embodied and/or implemented at least in part as a machine configured to receive a computer-readable medium storing computer-readable instructions. The instructions are preferably executed by computer-executable components preferably integrated with the system and one or more portions of the processor and/or the controller 430. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Although omitted for conciseness, the preferred embodiments include every combination and permutation of the various system components, operating modes, and/or method blocks.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

What is claimed is:

1. A wearable personal cooling and heating system for placement at a body region of a user, comprising:
a retention mechanism defining a lumen in a first configuration, the retention mechanism comprising:
a first layer comprising a plurality of first apertures,
a second layer comprising a plurality of second apertures aligned with the plurality of first apertures, and
a third layer comprising a thermally-conductive material, the third layer arranged adjacent to the body region of the user, wherein the first, second, and third layers are arranged in a stacked configuration;
a plurality of temperature modulation subsystems attached to the retention mechanism, wherein the plurality of temperature modulation subsystems are arranged in a circumferential array and disposed on the third layer, wherein, in the first configuration, the plurality of the temperature modulation subsystems are arranged at the body region of the user and a central axis of each of the plurality of first apertures and each of the plurality of second apertures is arranged at a nonzero angle with respect to a central axis of the lumen, each of the plurality of temperature modulation subsystems comprising:
a thermoelectric panel defining a first side and a second side opposing the first side, the thermoelectric panel of each of the plurality of temperature modulation subsystems extending through each of the plurality of first apertures and each of the plurality of second apertures and in thermal contact with the third layer of the retention mechanism at the first side, wherein the third layer extends past a footprint of each of the thermoelectric panels,
a heat sink in direct contact with the thermoelectric panel at the second side,
a shield, defining a shield cavity and an external surface, the external surface defining a set of airflow apertures, the shield attached to the thermoelectric panel and enclosing the heat sink within the shield cavity, and
a fan, arranged within the shield cavity between the heat sink and the external surface of the shield, and configured to actively drive airflow through the set of airflow apertures and along a flow path adjacent to the heat sink;
a control module, retained by the retention mechanism, communicatively coupled to the temperature modulation subsystem by way of a direct electrical connection routed between the first and second layers of the retention mechanism, wherein the temperature modulation subsystem is operable between a cooling mode and a heating mode by the control module, wherein the cooling mode comprises powering the thermoelectric panel with a first applied voltage having a first polarity and thereby generating a low temperature at the first side of the thermoelectric panel of each of the plurality of temperature modulation subsystems, and wherein the heating mode comprises powering the thermoelectric panel with a second applied voltage having a second polarity opposite the first polarity and thereby generating a high temperature at the first side of the thermoelectric panel of each of the plurality of temperature modulation subsystems.

2. The system of claim 1, wherein the retention mechanism defines a first edge and a second edge opposing the first edge, and further comprises a set of appendages that extend away from the first edge, the set of appendages defining the lumen in the first configuration, the set of appendages removably coupled to the retention mechanism proximal the second edge and configured to secure the retention mechanism in the first configuration at the body region of the user and thereby compress the body region of the user and arrange the temperature modulation subsystem at the body region of the user.

3. The system of claim 2, wherein the circumferential array comprises a pentagonal array.

4. The system of claim 1, wherein the low temperature is within the range of 49-61° Fahrenheit, and wherein the high temperature is within the range of 102-115° Fahrenheit.

5. The system of claim 1, further comprising a temperature sensor in direct thermal contact with at least one of the thermoelectric panels of the plurality of temperature modulation subsystems and communicatively coupled to the control module, wherein the cooling mode comprises maintaining the low temperature based on an output of the temperature sensor, and wherein the heating mode comprises maintaining the high temperature based on the output of the temperature sensor.

6. The system of claim 1, wherein the control module is communicatively coupled to a client application executing on a mobile device associated with the user, and wherein the plurality of temperature modulation subsystems is operable between the cooling mode and the heating mode based on instructions received from the user by way of the client application.

7. A wearable personal cooling and heating system for placement at a body region of a user, comprising:
a retention mechanism, wherein the retention mechanism further defines a lumen in a first configuration, and wherein the retention mechanism comprises:
a first layer defining an external side of the retention mechanism and further comprising a plurality of first apertures,
a second layer-defining an internal side and further comprising a plurality of second apertures; and
a third layer defining a coupling interface and further comprising a thermally-conductive material;
wherein the first layer, second layer, and third layer are arranged in a stacked configuration;
a plurality of temperature modulation subsystems, each of the plurality of temperature modulation subsystems coupled to the retention mechanism at the coupling interface, the plurality of temperature modulation subsystems arranged in a circumferential array, wherein, in the first configuration, a central axis of each of the plurality of first apertures and each of the plurality of second apertures is arranged at a nonzero angle with respect to a central axis of the lumen, each of the plurality of temperature modulation subsystems comprising:
a temperature-controllable substrate, wherein the temperature controllable substrate of each of the plurality of temperature modulation subsystem extends through each of the plurality of first apertures and each of the plurality of second apertures, and is in thermal contact with the third layer, a shield, defining a shield cavity, the shield arranged at the external side of the retention mechanism and coupled to the temperature-controllable substrate, and a heat exchanger in thermal contact with the temperature-controllable substrate and arranged within the shield cavity;

wherein the third layer extends past a footprint of each of the temperature controllable substrates;

a control module, retained by the retention mechanism, communicatively coupled to the temperature modulation subsystem, wherein the plurality of temperature modulation subsystem is operable between a cooling mode and a heating mode by the control module, wherein the cooling mode comprises generating a low temperature at the temperature-controllable substrate, and wherein the heating mode comprises generating a high temperature at the temperature-controllable substrate.

8. The system of claim 7, further comprising a thermally-conductive gel disposed between the temperature-controllable substrate and the third layer, wherein the third layer comprises a thermally-conductive fabric.

9. The system of claim 7, wherein the heat exchanger comprises a heat sink in direct contact with the temperature-controllable substrate.

10. The system of claim 9, wherein the shield further comprises an external surface defining a set of airflow apertures.

11. The system of claim 10, wherein the heat exchanger further comprises a fan, arranged within the shield cavity between the heat sink and the external surface of the shield, configured to actively drive airflow through the set of airflow apertures and along a flow path adjacent to the heat sink, and wherein the fan is mounted directly to the shield.

12. The system of claim 10, wherein each of the set of airflow apertures defines a hexagonal profile, and wherein the set of airflow apertures is arranged in a close-packed configuration.

13. The system of claim 7, wherein the temperature-controllable substrate comprises a thermoelectric panel.

14. The system of claim 7, wherein the retention mechanism defines a first side and a second side opposing the first side, and further comprises a set of appendages that extend away from the first side, the set of appendages defining the lumen in the first configuration, the set of appendages removably coupled to the second side and configured to secure the retention mechanism in the first configuration at a body region of a user and thereby compress the body region of the user and arrange the temperature modulation subsystem at the body region of the user.

15. The system of claim 14, wherein the array comprises a hexagonal array.

16. The system of claim 7, further comprising a temperature sensor in direct thermal contact with at least one of the temperature-controllable substrates of the plurality of temperature modulation subsystems and communicatively coupled to the control module, wherein the cooling mode comprises maintaining the low temperature based on an output of the temperature sensor, and wherein the heating mode comprises maintaining the high temperature based on the output of the temperature sensor.

17. The system of claim 16, wherein the low temperature is within the range of 49-61° Fahrenheit, and wherein the high temperature is within the range of 102-115° Fahrenheit.

18. The system of claim 7, wherein the control module is configured to modulate the temperature modulation subsystem between the cooling mode and the heating mode according to a predetermined pattern.

19. The system of claim 18, wherein the predetermined pattern is selected by the user at a client application executing on a mobile device in communication with the control module.

* * * * *